(12) United States Patent
Bai et al.

(10) Patent No.: US 12,109,177 B2
(45) Date of Patent: Oct. 8, 2024

(54) NEUTROPHIL SUPPRESSION AS PRECONDITIONING TO INCREASE ONCOLYTIC BACTERIAL THERAPY

(71) Applicant: The Johns Hopkins University, Baltimore, MD (US)

(72) Inventors: Renyuan Bai, Baltimore, MD (US); Verena Staedtke, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 18/085,467

(22) Filed: Dec. 20, 2022

(65) Prior Publication Data

US 2023/0201137 A1 Jun. 29, 2023

Related U.S. Application Data

(60) Provisional application No. 63/294,320, filed on Dec. 28, 2021.

(51) Int. Cl.
| | |
|---|---|
| *A61K 31/133* | (2006.01) |
| *A61K 31/535* | (2006.01) |
| *A61K 35/742* | (2015.01) |
| *A61K 45/06* | (2006.01) |
| *A61P 35/00* | (2006.01) |

(52) U.S. Cl.
CPC .......... *A61K 31/133* (2013.01); *A61K 31/535* (2013.01); *A61K 35/742* (2013.01); *A61K 45/06* (2013.01); *A61P 35/00* (2018.01)

(58) Field of Classification Search
CPC .................................................... A61K 31/133
See application file for complete search history.

(56) References Cited

U.S. PATENT DOCUMENTS

2022/0193149 A1* 6/2022 Manuel ................ A61K 48/005

OTHER PUBLICATIONS

Pinedo et al. (2000).*
McMahon et a. (2000).*

Bai et al., "Effective treatment of diverse medulloblastoma models with mebendazole and its impact on tumor angiogenesis", Neuro-oncology, 2015, 17(4):545-55.
Bai et al., "Prevention of tumor seeding during needle biopsy by chemotherapeutic-releasing gelatin sticks", Oncotarget, 2017, 8(16):25955-25962.
Bettegowda et al., "The genome and transcriptomes of the anti-tumor agent Clostridium novyi-NT", Nat Biotechnol, 2006, 24(12):1573-158.
Dang et al., "Targeting vascular and avascular compartments of tumors with C. novyi-NT and anti-microtubule agents", Cancer Biology & Therapy, 2004, 3(3):326-337.
Parvinian et al., "Development, growth, propagation, and angiographic utilization of the rabbit VX2 model of liver cancer: a pictorial primer and "how to" guide", Diagn Interv Radiol, 2014, 20(4):335-34.
Raleigh et al., "Relationship of hypoxia to metallothionein expression in murine tumors", Int J Radiat Oncol Biol Phys, 1998, 42(4):727-730.
Roberts et al., "Intratumoral injection of Clostridium novyi-NT spores induces antitumor responses", Sci Transl Med, 2014, 6(249):1-27.
Staedke et al., "Clostridium novyi-NT in cancer therapy", Genes Dis, 2016, 3(2):144-152.

* cited by examiner

*Primary Examiner* — Paul V Ward
(74) *Attorney, Agent, or Firm* — DLA Piper LLP (US)

(57) ABSTRACT

Provided herein are methods for increasing the therapeutic efficiency of oncolytic bacterial therapeutics. Bacterial oncolytic therapies, especially the ones targeting tumor hypoxia such as *C. novyi*-NT, often encounter incomplete tumor clearance in less hypoxic tumoral areas and severe inflammatory reactions. In this study, we explored immune-modulating preconditioning to suppress the host neutrophils and significantly enhanced the antitumor efficacy of *C. novyi*-NT in animal models, including an orthotopic brain tumor model in rabbits. The optimized preconditioning agent, hydroxyurea, is clinically approved and *C. novyi*-NT has demonstrated manageable safety and promising antitumor responses in clinical trials. Thus, the proposed preconditioning of neutrophil suppression is readily translatable to patients undergoing *C. novyi*-NT trials or other oncolytic biologic therapies and could improve outcome.

11 Claims, 12 Drawing Sheets

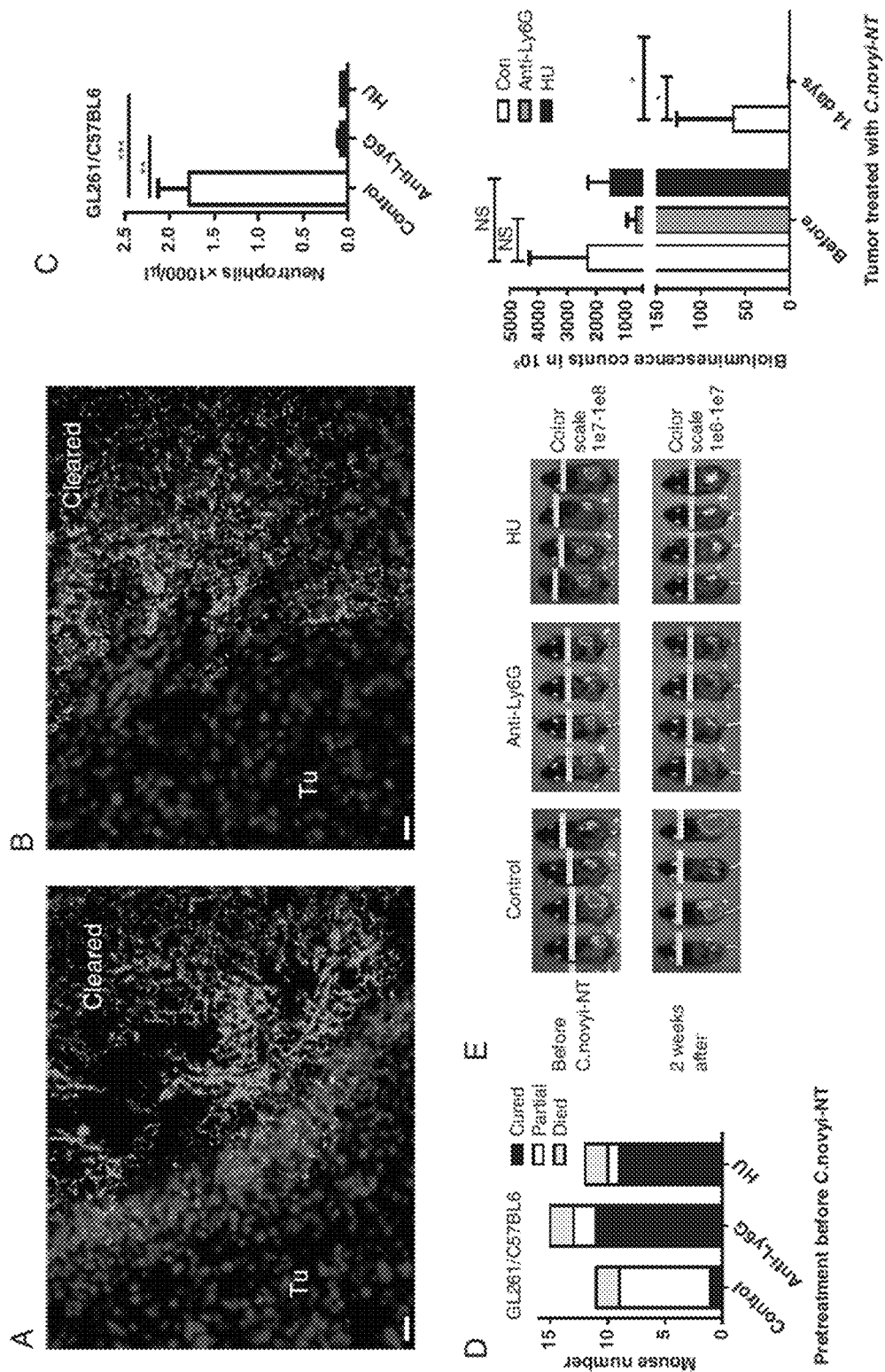
FIG. 1A-E

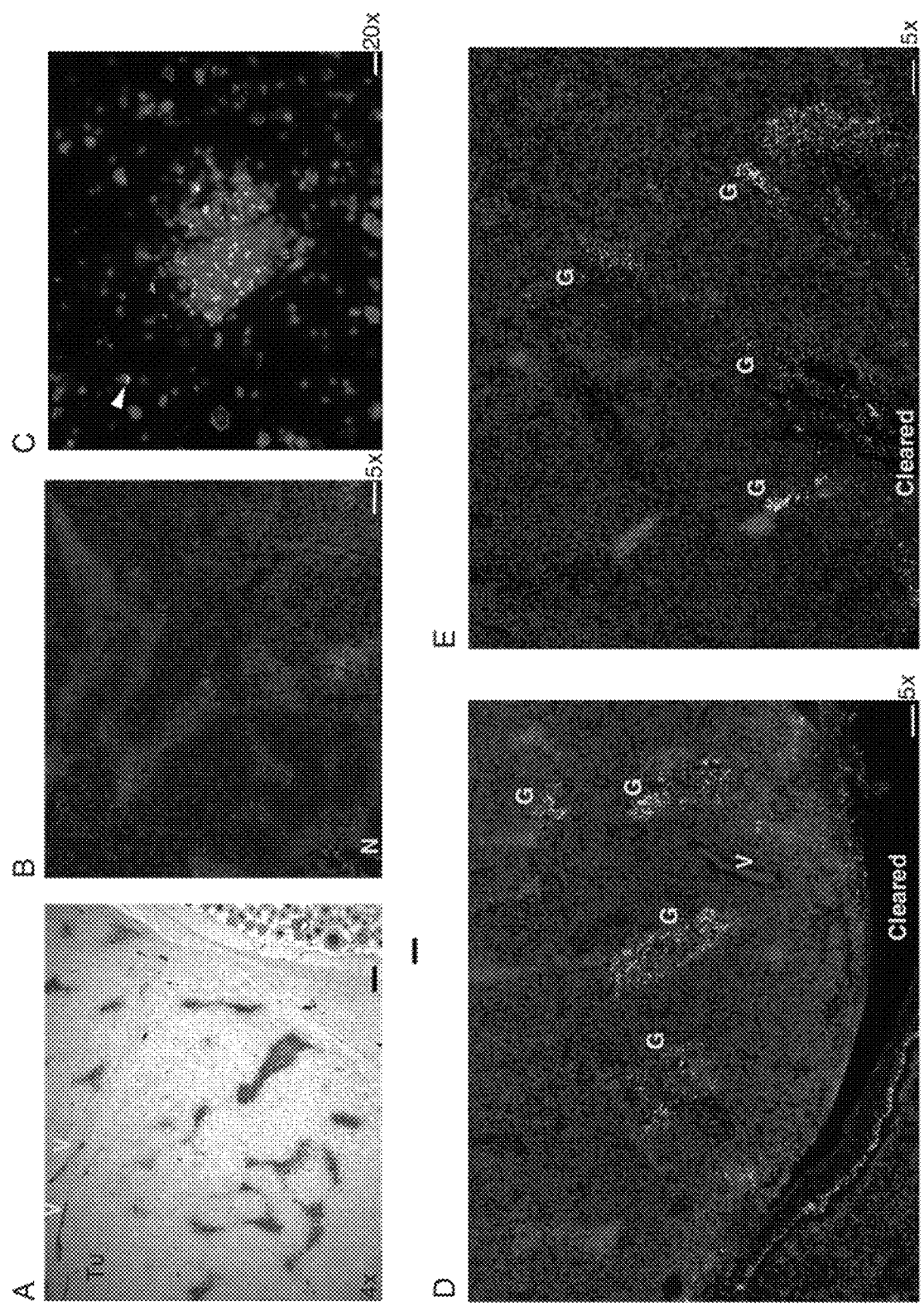
FIG. 2A-E

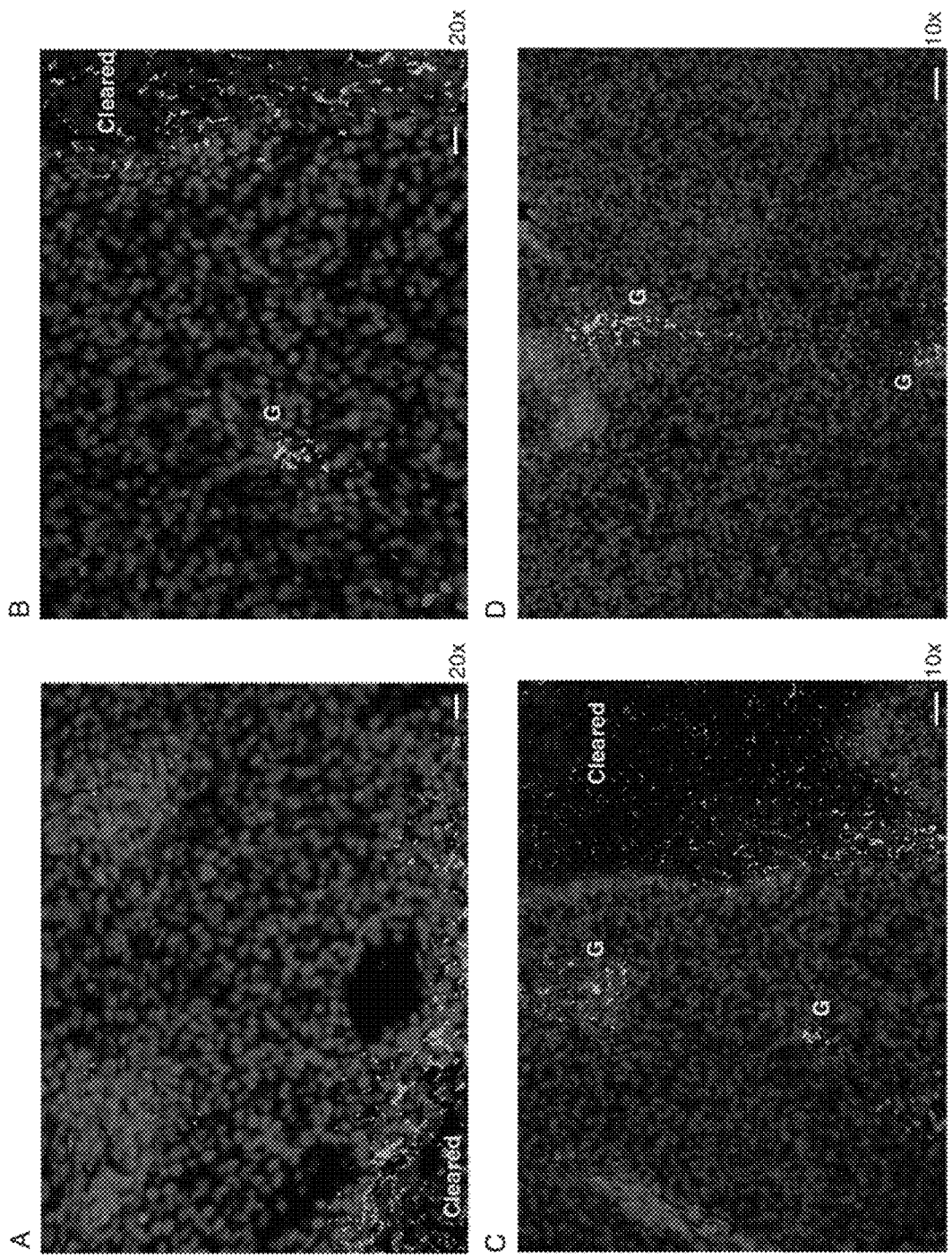
FIG. 3A-D

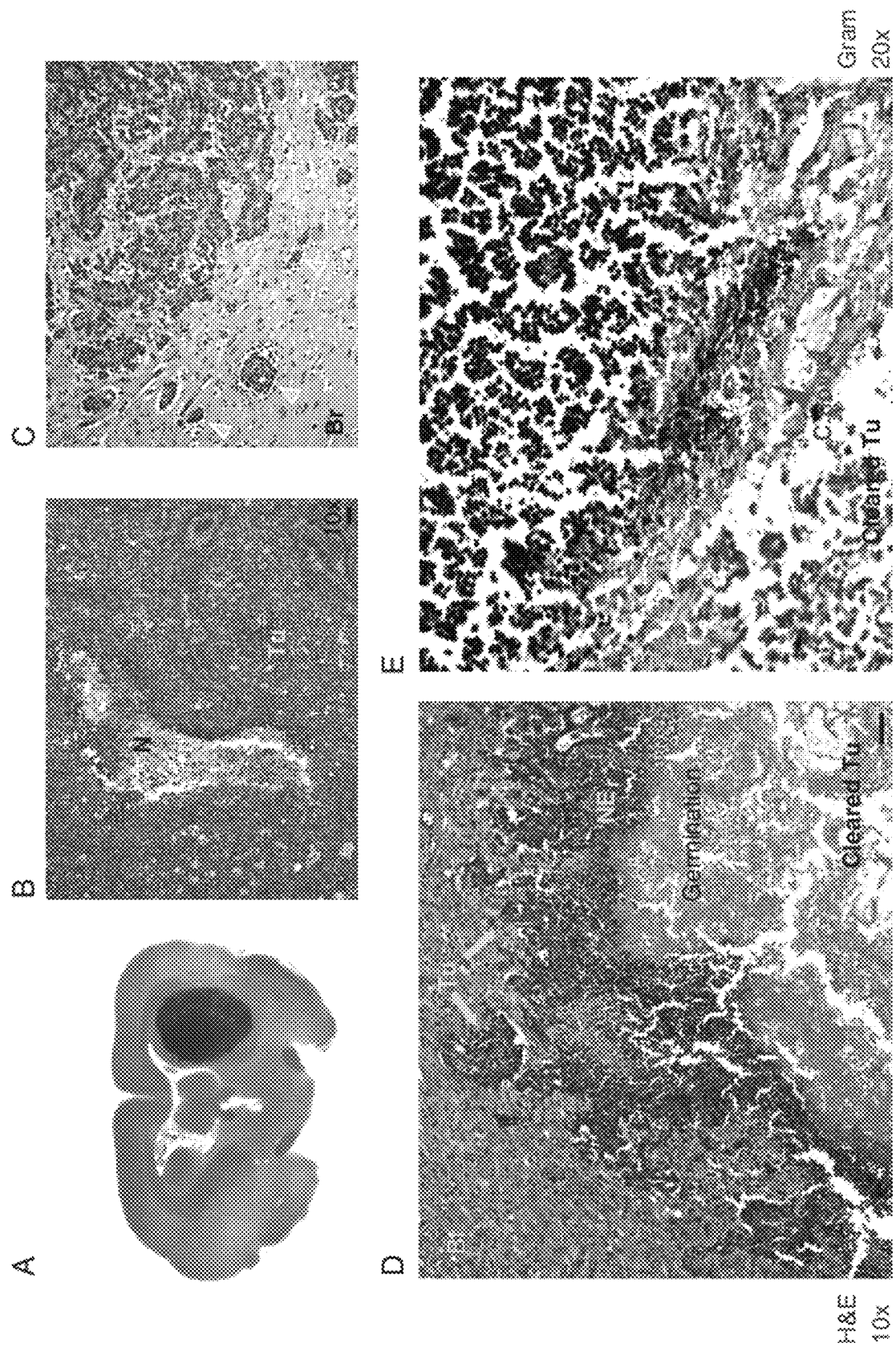
FIG. 4A-E

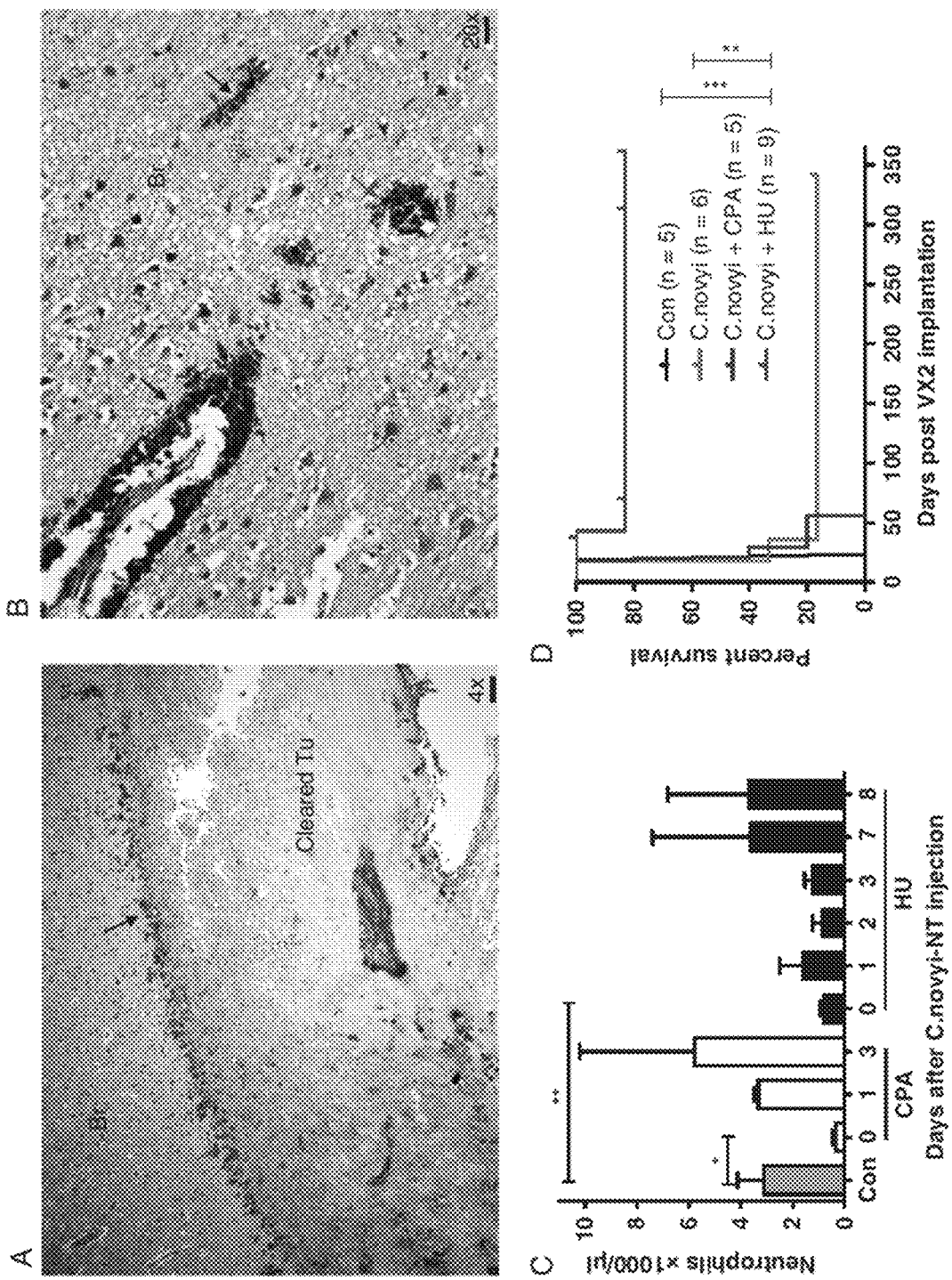
FIG. 5A-D

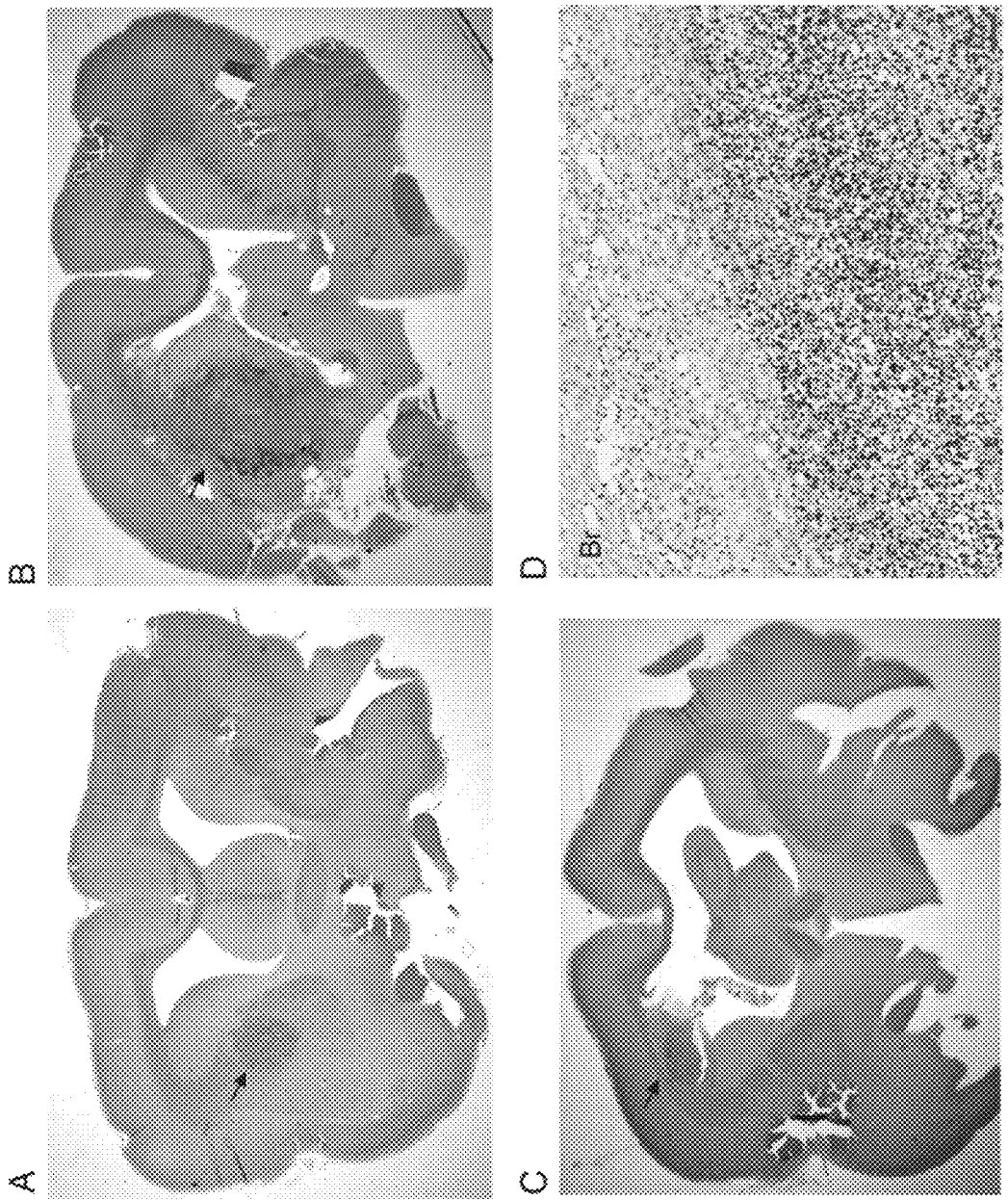
FIG. 6A-D

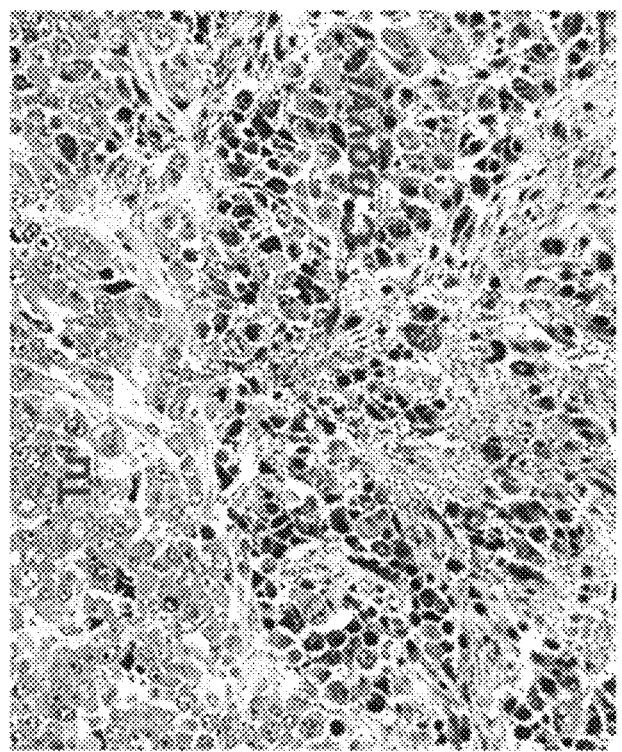
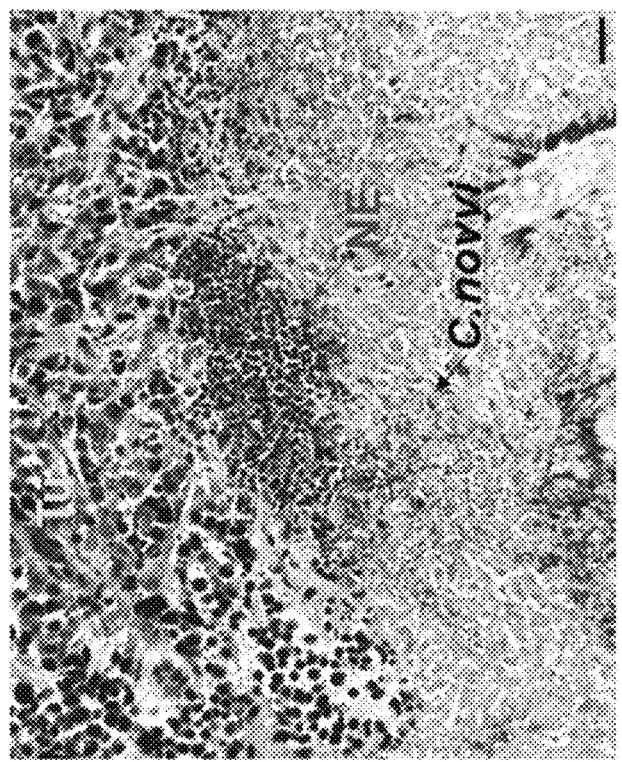
FIG. 7A-B

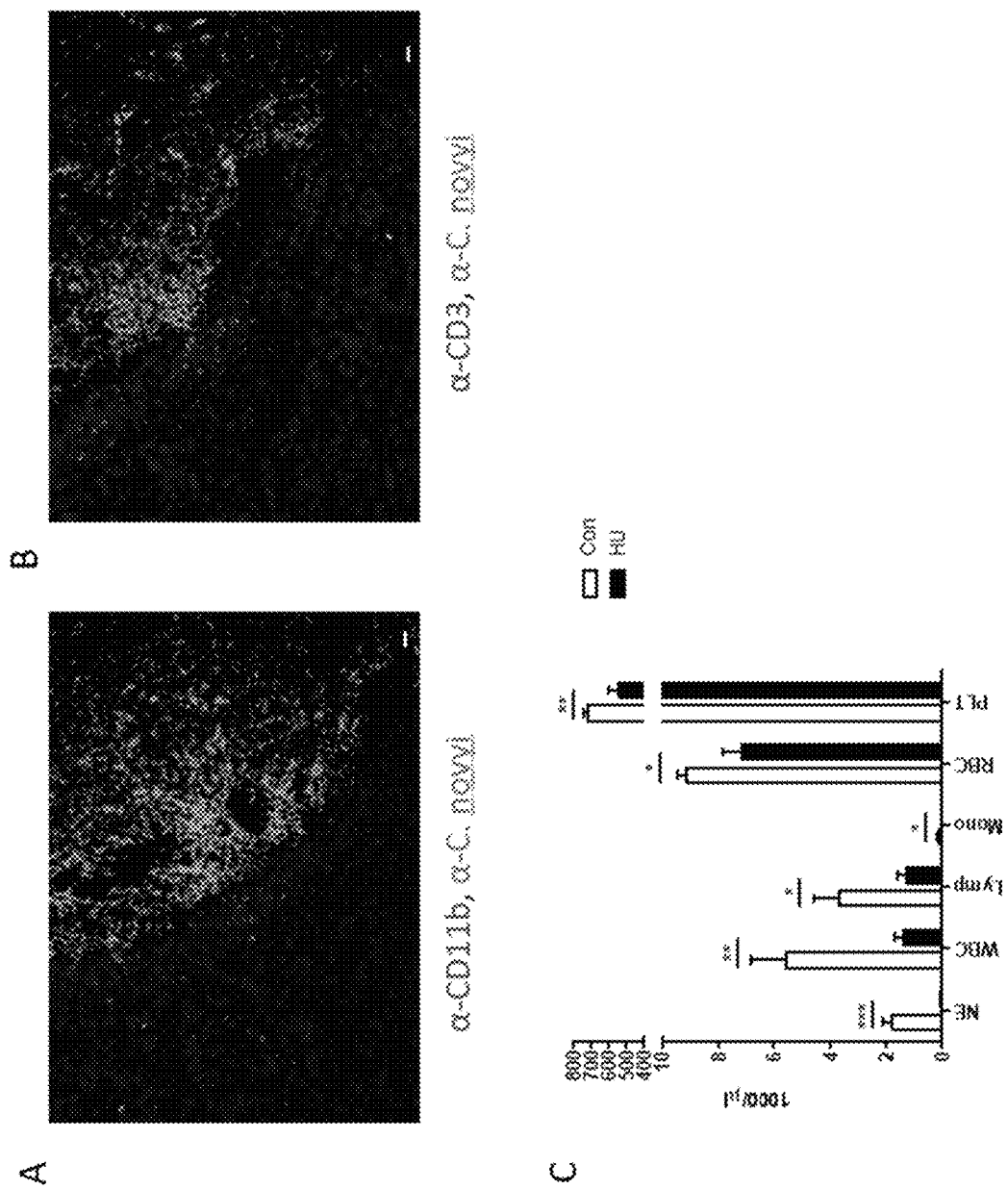
FIG. 8A-C

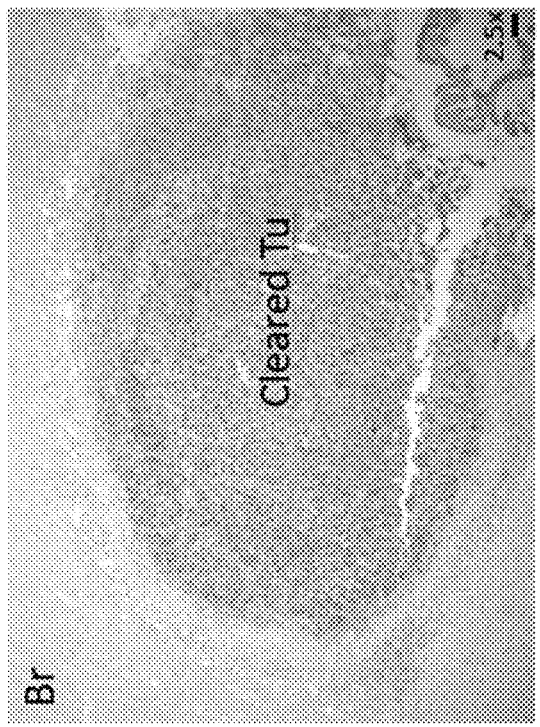
FIG. 11A-B

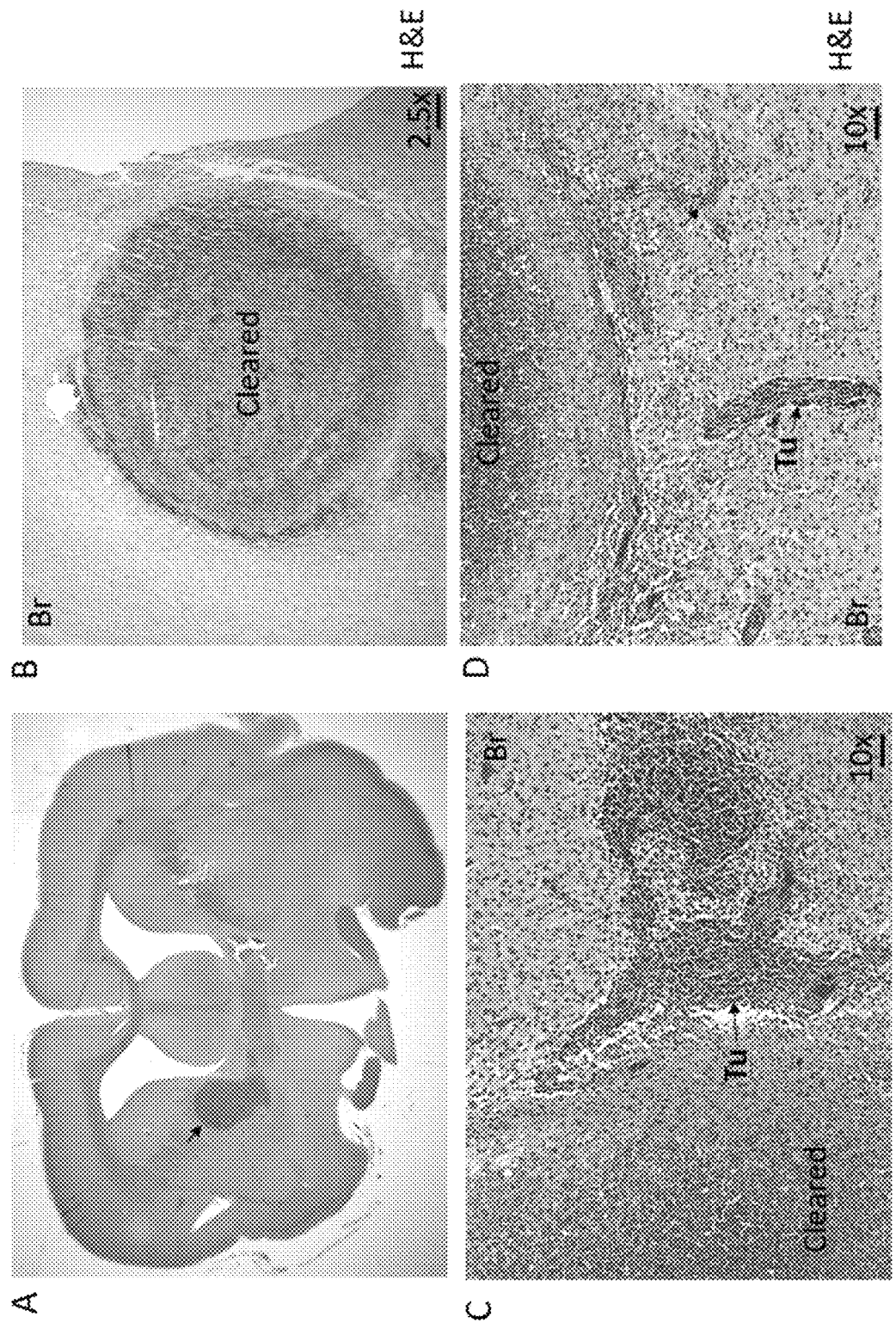
FIG. 12A-D

NEUTROPHIL SUPPRESSION AS PRECONDITIONING TO INCREASE ONCOLYTIC BACTERIAL THERAPY

CROSS-REFERENCE TO RELATED APPLICATIONS

This application claims the benefit under 35 USC § 119(e) of U.S. Provisional Application No. 63/294,320, filed Dec. 28, 2021, the content of which is herein incorporated by reference in their entirety.

STATEMENT REGARDING FEDERALLY SPONSORED RESEARCH OR DEVELOPMENT

This invention was made with government support under grant CA178118, CA196519, R25NS065729, 1K08CA230179, NS065729, and CA230179 awarded by the National Institutes of Health. The government has certain rights in the invention.

BACKGROUND OF THE INVENTION

Field of the Invention

The present invention relates generally to therapeutics and more specifically to methods of increasing the therapeutic efficiency of oncolytic bacterial therapeutics.

Background Information

Hypoxia in solid tumors is a major hindrance in cancer therapy, as most tumors, including the most aggressive brain tumor, glioblastoma, contain large, poorly vascularized hypoxic areas that limit the efficacy of radiation and chemotherapeutic drugs. However, the presence of hypoxia in solid tumors offers the potential for therapeutic anaerobic bacterial colonization in which anaerobic bacteria destroy the oxygen-low tumor tissue while sparing the well-oxygenated healthy tissues. A number of bacteria species in genera such as *Salmonella, Klebsiella, Escherichia, Caulobacter, Listeria, Bifidobacterium, Clostridium, Streptococcus, Lactobacillus, Mycobacterium* and *Proteus* have been developed as oncolytic bacteria. One successful strain is the anaerobic *Clostridium novyi*. The genus *Clostridium* was shown to cause tumor regression in rodent models, but a subsequent clinical failed to demonstrate any clinical benefit in humans that would outweigh the toxic effects. The inventors and others have shown that *C. novyi*-NT can selectively germinate and grow in the hypoxic regions of solid tumors after intravenous injection with less toxicity. More recently, the inventors showed that intratumoral injection of *C. novyi*-NT spores may be a promising approach to facilitate germination and reduce spore dosage needed for germination (Staedke et al. 2016, Dang et al. 2004). This concept has been reevaluated using the attenuated *C. novyi*-NT strain, which is characterized by a deletion of the lethal toxin gene rendering the bacterium less toxic. However, the challenges of *C. novyi*-NT cancer therapy remain to be substantial with severe host inflammatory responses and reduced efficacy in clearing up tumor outer rims. There is an unmet need for methods of improving tumor clearance and reducing treatment-related toxicities.

SUMMARY OF THE INVENTION

The present invention is based on the seminal discovery that neutrophil accumulation in tumors with germinating bacteria may contribute to blockage preventing certain anaerobic bacteria, for example, *C. novyi*-NT, from complete tumor clearance. Further, hydroxyurea was identified as an effective suppressor of neutrophils to overcome this problem, which enhances the tumor clearance and reduces alternative treatment-related toxicities.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

All publications, patents, and patent applications mentioned in this specification are herein incorporated by reference to the same extent as if each individual publication, patent, or patent application was specifically and individually indicated to be incorporated by reference.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, it will be understood that modifications and variations are encompassed within the spirit and scope of the instant disclosure. The methods and materials are now described herein.

The terms "subject", "patient", or "subjects" as used herein, refer to a human or other animal, including rodents, ungulates, or mammals; for example, horses, cattle, sheep, pigs, goats, llama, camel, dogs, cats, birds, ferrets, rabbits, squirrels, mice, rats, or ferrets. In some embodiments, the subject is a human subject.

The terms "treat" or "treatment as used herein, refers to methods of treating a cancer, which methods include the administration of at least one compound or composition, at one or multiple dosages and times of administration, which reduce the frequency of, delay the onset of, or reduce the intensity of, symptoms of a medical condition or reduce the size of, density of, or volume of hypoxic regions of a cancer or tumor relative to a subject not receiving the compound or composition. This can also include reducing, reversing, easing, or arresting the symptoms, clinical presentation, or physiological responses to treatment, related treatments, or co-administered treatments.

The term "effective amount" refers to the amount of a compound, composition, or formulation that is sufficient to treat a condition or disease, to produce desirable effects or results, or to reduce, ease, or arrest symptoms of a condition or disease. "Effective amount" is used interchangeably with the term "therapeutically effective amount".

In some embodiments described herein, the compounds or formulations are administered by various routes, including parenteral or systemic, oral, topical, intravenous, intramuscular, subcutaneous, or intratumoral routes.

In some embodiments, the presently disclosed subject matter provides methods for treating solid tumors using bacteria, bacterial products, and/or other immunomodulatory agents. In some embodiments, the bacterium or bacterial product thereof is an anaerobic bacterium or bacterial product thereof. Suitable genera include, but are not limited to, *Salmonella, Klebsiella, Escherichia, Caulobacter, Listeria, Bifidobacterium, Clostridium*, such as *Clostridium novyi* or *Clostridium sordellii* (*C. sordellii*), *Streptococcus, Lactobacillus, Mycobacterium* and *Proteus*. In some embodiments, the bacterium or bacterial product thereof is an obligate anaerobic bacterium or bacterial product thereof. As used herein, "anaerobic bacteria" are bacteria that do not require oxygen for growth. As used herein, an "obligate anaerobic bacterium" is a bacterium that not only requires oxygen for growth but is also harmed by normal levels of atmospheric oxygen. In some aspects, the anaerobic bacterium or bacterial product thereof is *Clostridium novyi* or bacterial product thereof.

In some embodiments, the bacterium or bacterial product thereof is a toxin-depleted anaerobic bacterium or bacterial product thereof. In one aspect, the toxin-depleted anaerobic bacterium or bacterial product thereof is *Clostridium novyi*-NT (*C. novyi*-NT) or bacterial product thereof.

Immunomodulatory agents can include, for example, hydroxyurea (HU), cyclophosphamide, an antibody having the binding specificity of 1A8 anti-Ly6G (Ly-6G Monoclonal Antibody (1A8-Ly6g), APC, eBioscience™), and the like. In some aspects, immunomodulatory agents can be administered to a subject in need thereof for neutrophil depletion.

In some embodiments, other immunomodulatory agents can be combined with administration of hydroxyurea (HU), cyclophosphamide, or a combination thereof. Such other immunomodulatory agents can include, for example, immunostimulatory cytokines such as GM-CSF, interleukin-12 (IL-12), and IL-15. Other immunomodulatory agents include prednisone, methylprednisolone, dexamethasone, colchicine, hydroxychloroquine, sulfasalazine, dapsone, and azathioprine. Additional examples of bacterial products used for immunostimulatory purposes include inactivated bacteria or bacterial components such as Freund's complete adjuvant and Coley's toxin. Further, the use of HU, for example, may reduce the amount of a chemotherapeutic agent needed to treat a subject.

In some embodiments, the techniques described herein relate to a method of treating cancer in a subject including: a) administering to the subject hydroxyurea (HU), cyclophosphamide, or a combination thereof: and b) an anaerobic bacterium, thereby treating cancer in the subject.

In some embodiments, the techniques described herein relate to a method for stimulating tumoricidal activity in a subject including: a) administering to the subject hydroxyurea (HU), cyclophosphamide, or a combination thereof; and b) an anerobic bacterium, thereby stimulating tumoricidal activity in the subject.

In further embodiments, the techniques described herein relate to a method for treating a solid tumor in a subject including: a) administering to the subject hydroxyurea (HU), cyclophosphamide, or a combination thereof, and b) an anerobic bacterium, thereby treating the solid tumor in the subject.

In certain embodiments of the method described herein, the anaerobic bacterium is *Clostridium novyi*. In some embodiments herein, the anaerobic bacterium is a toxin-depleted anaerobic bacterium. In certain embodiments described herein, the toxin-depleted anaerobic bacterium is *Clostridium novyi*-NT (*C. novyi*-NT).

In some embodiments of the method described herein, a combination of the hydroxyurea (HU), the cyclophosph-amide, or a combination thereof and the anerobic bacteria is administered sequentially. In further embodiments, the hydroxyurea (HU), cyclophosphamide, or a combination thereof and the anerobic bacteria is administered concurrently.

In additional embodiments described herein, the method further including administering the hydroxyurea (HU), cyclophosphamide, or combinations thereof from about 10-72 hours prior to administering the anaerobic bacterium. In some embodiments, the administration is from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, or 72 hours prior to administering the anaerobic bacterium.

In some embodiments of the method of treating cancer described herein, the cancer is glioblastoma (GBM). In further embodiments, a subject has glioblastoma (GBM).

In some aspects, at least one member of the group consisting of bacteria, bacterial products, and immunomodulatory agents (e.g., HU, cyclophosphamide) is administered intravenously or intratumorally. In other aspects, the at least one antibody is administered by at least one method selected from the group consisting of intravenous, intramuscular, subcutaneous, and intratumoral.

The methods described herein can include administering or implanting *C. novyi*-NT spores to a subject in need thereof.

In some embodiments, the techniques described herein relate to a method of treating cancer in a subject including: (a) administering to the subject at least one immunoregulatory compound; and (b) administering at least one anaerobic species of bacteria, thereby treating cancer in the subject. In further embodiments, the cancer is a solid tumor. In various embodiments, the cancer is brain, colon, breast, prostate, liver, kidney, lung, esophagus, head and neck, ovary, cervix, stomach, colon, rectum, bladder, uterus, testis, or pancreatic cancer. In certain the cancer is brain cancer.

In some embodiments, the method described herein relates to a method of treating cancer, including administering to the subject an immunoregulatory compound. The immunoregulatory compound can be cyclophosphamide, hydroxyurea, prednisone, methylprednisolone, dexamethasone, colchicine, hydroxychloroquine, sulfasalazine, dapsone, or azathioprine. In some aspects, the immunoregulatory compound is infliximab, adalimumab, golimumab, etanercept, certolizumab, tocilizumab, sarilumab, eculizumab, secukinumab, ixekizumab, brodalumab, or guselkumab.

In certain embodiments, the immunoregulatory compound is administered to the subject from about 1, 2, 3, 4, 5, 6, 7, 8, 9, or 10 days prior to administering the anaerobic species of bacteria. In some embodiments, the immunoregulatory compound is administered from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, or 72 hours prior to administering the anaerobic bacterium. In further embodiments, the immunoregulatory compound is administered to the subject at a reduced dose for about 1, 2, 3, 4, 5, 6, 7, 8, 9, or 10 days after administering the anaerobic species of bacteria. In various embodiments, the immunoregulatory compound is administered to the subject for about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, or 72 hours after administering the anaerobic species of bacteria.

In some embodiments described herein, the immunoregulatory compound is cyclophosphamide. In further embodiments, the cyclophosphamide is administered at a daily dose of about 0.1 to 125 mg/kg, 1-125 mg/kg, 1-100 mg/kg, 1-50 mg/kg, 1 mg/kg, 10 mg/kg, 20 mg/kg, 25 mg/kg, 30 mg/kg, 40 mg/kg, 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, about 105 mg/kg, about 110 mg/kg, about 115 mg/kg, about 120 mg/kg, or about 125 mg/kg. In additional embodiments, the cyclophosphamide is administered with at least one antineoplastic detoxifying agent, to mitigate potential urotoxicity of other compounds administered to the patient. In various embodiments, the antineoplastic detoxifying agent is Mesna. In some embodiments herein, the Mesna is administered at a daily dose of about 1 mg/kg, 10 mg/kg, 20 mg/kg, about 25 mg/kg, about 30 mg/kg, about 35 mg/kg, about 40 mg/kg, about 45 mg/kg, or about 50 mg/kg.

In some embodiments disclosed herein, the method of treating cancer described herein includes administering to the subject an immunoregulatory compound, the immunoregulatory compound is hydroxyurea. In certain embodiments, the hydroxyurea is administered at a daily dose of about 0.01-500 mg/kg, from about 0.1-500 mg/kg, from about 1-500 mg/kg, from about 1-250 mg/kg, about 1-200 mg/kg, about 1-150 mg/kg, about 1-100 mg/kg, about 1-50 mg/kg, about 1-25 mg/kg, about 1-20 mg/kg, about 1-15 mg/kg, about 1-10 mg/kg, about 1-5 mg/kg, about 0.1-20 mg/kg, about 100 mg/kg, about 110 mg/kg, about 120 mg/kg, about 130 mg/kg, about 140 mg/kg, about 150 mg/kg, about 160 mg/kg, about 170 mg/kg, about 180 mg/kg, about 190 mg/kg, about 200 mg/kg, about 210 mg/kg, about 220 mg/kg, about 230 mg/kg, about 240 mg/kg, about 250 mg/kg, about 260 mg/kg, about 270 mg/kg, about 280 mg/kg, about 290 mg/kg, about 300 mg/kg, about 310 mg/kg, about 320 mg/kg, about 330 mg/kg, about 340 mg/kg, about 350 mg/kg, about 360 mg/kg, about 370 mg/kg, about 380 mg/kg, about 390 mg/kg, about 400 mg/kg, about 410 mg/kg, about 420 mg/kg, about 430 mg/kg, about 440 mg/kg, about 450 mg/kg, about 460 mg/kg, about 470 mg/kg, about 480 mg/kg, about 490 mg/kg, or about 500 mg/kg.

In various embodiments, the techniques described herein relate to a method of treating cancer which includes administering at least one anaerobic species of bacteria, wherein the bacteria is *Salmonella* ssp., *Klebsiella* ssp., *Escherichia* ssp., *Caulobacter* ssp., *Listeria* ssp., *Bifidobacterium* ssp., *Clostridium* ssp., *Streptococcus* ssp., *Lactobacillus* ssp., *Mycobacterium* ssp., or *Proteus* ssp. In certain embodiments disclosed herein, the at least one anaerobic species of bacteria is *Clostridium novyi* or *Clostridium sordellii*. Additionally, in some embodiments herein, the anaerobic species of bacteria is *Clostridium novyi*. Additional embodiments include a method wherein the at least one anaerobic species of bacteria is a toxin-depleted species of anaerobic bacteria. In various embodiments described herein, the toxin-depleted species of anaerobic bacteria is *C. novyi*-NT.

In some aspects of the method described herein, an effective amount of *C. novyi*-NT spores is administered to the patient by injection into the tumor.

In further embodiments, an immunoregulatory compound is injected subcutaneously at the time of spore injection to minimize the risk of edema. In some embodiments the immunoregulatory compound is dexamethasone sodium phosphate, azathioprine, or a combination thereof.

In any embodiment disclosed herein, the anaerobic species of bacteria is administered in combination with drugs used in chemotherapy, including Carboplatin, Cisplatin, Cyclophosphamide, Docetaxel, Doxorubicin, Etoposide, Fluorouracil, Gemcitabine, Methotrexate, Paclitaxel, Erlotinib, Imatinib mesylate, Irinotecan, Sorafinib, Sunitinib, Topotecan, Vincristine, Vinblastine, Rituximab, or others.

In some embodiments of the method of treating cancer described herein, the *C. novyi*-NT spores are administered at a concentration of $6\times10^6/\mu l$, $2\times10^6/\mu l$, $3\times10^6/\mu l$, $4\times10^6/\mu l$, $5\times10^6/\mu l$, $6\times10^6/\mu l$, $7\times10^6/\mu l$, $8\times10^6/\mu l$, $9\times10^6/\mu l$, or $10\times10^6/\mu l$. In certain embodiments, the *C. novyi*-NT spores are administered at a concentration of $6\times10^6/\mu l$. In some embodiments, the volume of *C. novyi*-NT spores administered is 1 µl, 2 µl, 3 µl, 4 µl, or 5 µl. In other embodiments, the *C. novyi*-NT spores are administered to one, two, three or more locations in the tumor. In various aspects, the *C. novyi*-NT are administered via injection into the tumor.

BRIEF DESCRIPTION OF THE DRAWINGS

FIGS. 1A-E show neutrophil barriers prevented tumor clearance by *C. novyi*-NT in a subcutaneous mouse tumor model. FIG. 1A shows flank GL261 tumor was injected intratumorally with *C. novyi*-NT spores and harvested 12 hr later, fixated and stained with anti-Ly6G (1A8, medium grey) and anti-*C. novyi* (light grey) antibodies. Neutrophils were shown of forming a barrier between the tumor and germinating *C. novyi*-NT. Cleared: area where tumor cells were completely eradicated. Scale bar: 20 µm. FIG. 1B shows mouse bearing flank GL261 tumor was treated with anti-Ly6G antibody intraperitoneally (IP) 24 hours prior to the injection of *C. novyi*-NT spores. Tumor was harvested and stained as described in A. Neutrophil accumulation was not observed with the germinating bacteria. Scale bar: 20 µm. FIG. 1C shows blood neutrophil count in GL261 tumor-bearing mice treated with anti-Ly6G antibody (48 h) or HU (5 days) were measured and compared with the untreated control mice, showing the treatments greatly suppressed the neutrophil levels. n=3. FIG. 1D shows efficacies of intratumoral *C. novyi*-NT treatment in flank GL261 tumor. Suppressing neutrophils via anti-Ly6G or HU significantly reduced the partial tumor clearance and improved the total tumor clearance (cured). The occurrence of treatment-related death remained similar among the groups (died). FIG. 1E shows an example of bioluminescence monitoring of luciferase-labeled flank GL261 tumors in different treatment groups as described in D (left panels). Bioluminescence counts were quantified and analyzed for statistical significance using T test (right graph). n=4.

FIGS. 2A-E show distribution of tumor hypoxic areas and *C. novyi*-NT germination. FIGS. 2A-B show mice bearing flank GL261 tumor were injected with pimonidazole (PMD) 60 min before harvesting. Hypoxia was visualized by immunohistochemistry (IHC, dark grey) in FIG. 2A or immunofluorescence (IF, medium grey) via the mouse Hypoxiprobe antibody in FIG. 2B. Hypoxic pockets were observed in the tumor outer rim area. S: surrounding tissue. Scale bar: 100 µm. FIG. 2C shows a presumed injection site of *C. novyi*-NT spores was analyzed by anti-PMD Hypoxyprobe-1 antibody (medium grey dots), anti-*C. novyi* antibody (light grey dots) and DAPI (light grey in center). A mix of spore (small round) and germinated (rod) forms of *C. novyi*-NT was observed. The white arrow head indicated a germinated *C. novyi*-NT within a hypoxic tumor cells. Scale bar: 20 µm. FIGS. 2D-E Macroscopic views of *C. novyi*-NT germination in flank GL261 tumor labeled with PMD and pretreated with anti-Ly6G 24 hrs before. IF staining showed germination (G, light grey) largely occurred within the tumor hypoxic areas (red). Red blood cells in the vessels also appeared red. Cleared: area where tumor cells were completely eradicated. V: blood vessels. Scale bar: 100 µm.

FIGS. 3A-D show spreading of the *C. novyi*-NT germination in the tumor followed the tumor hypoxic areas. FIG. 3A shows spreading of individual *C. novyi*-NT bacteria (light grey dots and rods) in the tumor body adjacent to a main germination pocket clear of tumor cells (cleared). Scale bar: 20 μm. FIG. 3B shows germination (G, light grey) occurred within a hypoxic area adjacent to a main germination pocket cleared of tumor cells (cleared). Scale bar: 20 μm. FIGS. 3C-D show germination (G, light grey) within the hypoxic areas within a tumor. A germinating area free of tumor cells (cleared) was shown in C, with adjacent smaller hypoxic pockets containing germinating bacteria (G, light grey). Scale bar: 50 μm.

FIGS. 4A-E show neutrophil barriers restricted the spread of *C. novyi*-NT in the VX2 rabbit brain tumor. FIG. 4A shows H&E staining of a coronal section of a rabbit brain at day 19 after VX2 tumor implantation. Tumor was stained blue in the right frontal lobe. FIG. 4B shows H&E staining of the VX2 brain tumor showed dense tumor cells with a necrotic area (N). Scale bar: 50 μm, FIG. 4C shows invading tumor cells (white arrow heads) in the brain tissue (Br) were observed around the rim of VX2 brain tumor in the H&E stained section. This resembles the invasive feature of human glioblastomas. Scale bar: 50 μm. FIG. 4D shows areas of *C. novyi*-NT germination were surrounded by neutrophil layers in the tumor main body that has been cleared of tumor cells (cleared Tu). Scale bar: 50 μm. FIG. 4E shows a front of germinating *C. novyi*-NT (blue) visualized by gram staining was blocked by a layer of neutrophils (NE). Scale bar: 50 μm.

FIGS. 5A-D show neutrophil suppression improved the efficacy and safety in rabbit VX2 brain tumor model. FIG. 5A shows a macroscopic view of a germinating front (blue, Gram staining) of *C. novyi*-NT and cleared tumor main body in the rabbit VX2 brain tumor 72 hrs after spore injection. Scale bar: 100 μm. FIG. 5B shows a germinating *C. novyi*-NT in the suspected invading tumor blood vessels (black arrows) and satellites (grey arrow) in the rabbit brain (Br). Scale bar: 20 μm. FIG. 5C shows comparing neutrophil suppression by cyclophosphamide (CPA) and hydroxyurea (HU) by measuring the blood neutrophil counts before and after *C. novyi*-NT spore injection. The baseline neutrophil level without pretreatment was used as control (n=4). Neutrophil levels rebounded 3 days after the *C. novyi*-NT treatment, compared with 1 day in the CPA-pretreated group. FIG. 5D shows neutrophil suppression via HU pretreatment greatly improved tumor clearance and reduced treatment-related toxicity of *C. novyi*-NT in VX2 brain tumor model. Rabbit survival data of control, intratumorally injected *C. novyi*-NT spore alone, *C. novyi*-NT spores with CPA pretreatment, and *C. novyi*-NT spores with HU pretreatment were plotted in Kaplan-Meier survival curves. Median survival: Con=21 days, *C. novyi*-NT=18 days, *C. novyi*-NT+CPA=21 days. Death time: Con (n=5): day 19, 20, 21, 22, 23; *C. novyi*-NT (n=6): day 18, 18, 18, 18, 36, 1 long-term survivor; *C. novyi*-NT+CPA (n=5): day 18, 20, 21, 29, 56; *C. novyi*-NT+HU (n=9): day 43, 8 long-term survivors.

FIGS. 6A-D show a macroscopic overview of *C. novyi*-NT treated VX2 tumor in the rabbit brain. FIG. 6A shows H&E staining of a VX2 tumor at the day of *C. novyi*-NT treatment. Tumor was implanted in the right frontal lobe (black arrow). FIG. 6B shows VX2 tumor was stained by H&E after the treatment related death one day post the *C. novyi*-NT spore injection. Severe inflammatory reaction was observed around the tumor site featured by widespread hemorrhage (black arrow). FIGS. 6C-D show a rabbit brain was harvested 8 days after the *C. novyi*-NT spores injection in a HU-pretreatment rabbit while the animal was in a healthy condition, and stained with H&E or IHC of neutrophil enzyme MPO. The germination area showed a restrained pattern (black arrow, FIG. 6C) and no tumor cells were observed in the rim of the cleared tumor body. A tear of the section was indicated by the grey arrow. Anti-MPO IHC showed that the space was filled with neutrophils (dark grey, FIG. 6D). Scale bar: 50 μm.

FIGS. 7A-B show the effects of tumor treatment with 1A8 antibody. A flank GL261 tumor injected with *C. novyi*-NT spores and harvested 24 hrs after the spore injection, and Gram stained with safranin counter-staining. These Figures demonstrate germinating bacteria (dark grey) and marked accumulation of polymorphonuclear granulocytes between the germinating bacterial and remaining tumor rim. Tu: tumor. NE: neutrophil. Scale bar: 50 μm. FIG. 7B shows polymorphonuclear granulocytes depleted by treating the mice with 1A8 antibody intraperitoneally (IP) 24 hrs before the spore injection, shown by the Gram staining where the bacteria (dark grey) penetrated the tumor rim freely. Scale bar: 20 μm.

FIGS. 8A-C show the effect of effects of tumor treatment with HU. FIGS. 8A-B shows a flank GL261 tumor injected with *C. novyi*-NT spores and harvested 24 hrs after the spore injection. *C. novyi*-NT was stained green (light grey in the Figures) and staining with anti-CD11b (macrophages and monocytes) and anti-CD3 (T cells) antibodies (grey) revealed minimal positive cells among the immune cell accumulation. Scale bar: 20 μm. FIG. 8C shows blood counts of mice treated with HU (n=3). HU treatment drastically reduced the neutrophil counts, while other blood cells were also affected in various degrees by HU.

FIG. 9 shows tumor blood vessels. A flank GL261 tumor was labelled with pimonidazole (PMN) via IP injection 90 min before harvesting, and immunohistochemistry staining of PMN shows positive staining (dark grey) of tumor blood vessel structures. This is a higher magnification (20×) of FIG. 8A. Scale bar: 20 μm.

FIG. 10 shows cell type counts after treatment with HU. Rabbits were treated with HU for 5 days and blood cell counts were compared with the control rabbits (n=3). HU treatment induced a significant reduction of neutrophil counts, and in lesser degree also the platelets, but has not affected other blood cell types significantly.

FIGS. 11A-B show treatment effects on a brain tumor. FIG. 11A shows a macroscopic overview of former brain tumor area of rabbit treated with HU and *C. novyi*-NT spores and harvested 8 days after the treatment in a healthy condition. Section was stained with anti-MPO antibody (dark grey) and showed the lesion was filled with neutrophils. Scale bar: 100 μm. FIG. 11B shows an H&E staining of this brain section, showing tumor was cleared 8 days following *C. novyi*-NT treatment. Scale bar: 50 μm.

FIGS. 12A-D show a rabbit treated by *C. novyi*-NT alone that survived the initial germination and sacrificed at healthy condition 8 days after the spore injection. FIG. 12A shows a macroscopic view of the coronal H&E section of the brain with a restricted lesion (black arrow). FIG. 12B shows the brain section stained with anti-MPO IHC, a neutrophil enzyme. The lesion was filled predominantly with neutrophils without germinating bacteria. Cleared: area where tumor cells were completely eradicated. Scale bar: 200 μm. FIGS. 12C and D shows growing tumor cells were observed in the former tumor-brain transition areas, indicating a partial clearance of the tumor. Scale bar: 50 μm.

DETAILED DESCRIPTION OF THE INVENTION

Figure 9:
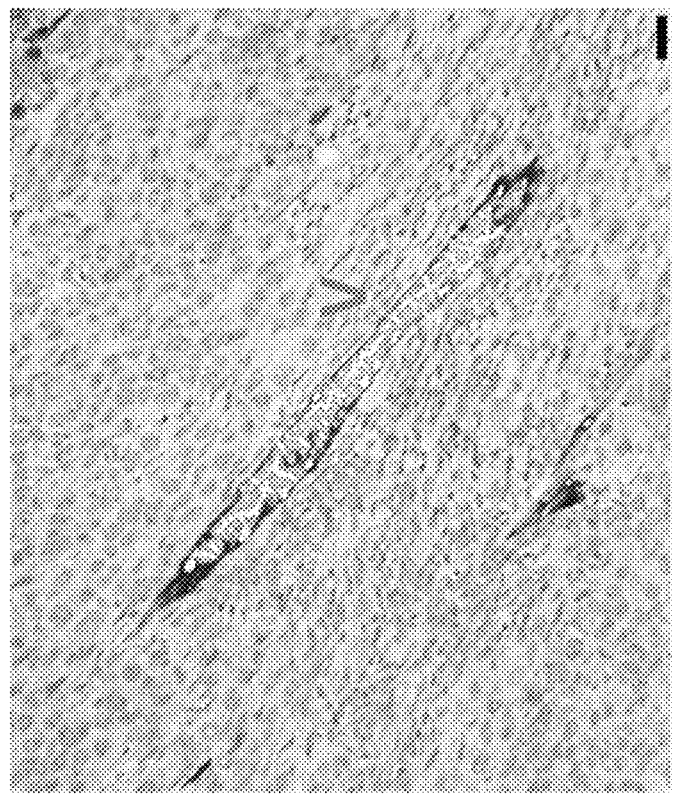

The present invention is based on the seminal discovery that neutrophil accumulation in tumors with germinating bacteria may contribute to blockage preventing certain anaerobic bacteria, for example, *C. novyi*-NT, from complete tumor clearance.

Hypoxia is a prominent feature of solid tumors and can function as fertile environment for oncolytic anaerobic bacteria such as *Clostridium novyi*-NT (*C. novyi*-NT) where it can induce tumor destruction in mice and patients. However, two major obstacles have limited its use, namely the host inflammatory response and the incomplete clearance of normoxic tumor areas. In this study we used a subcutaneous tumor model of a glioblastoma (GBM) cell line in immunocompetent mice to investigate the local distribution of tumor hypoxia, kinetics of *C. novyi*-NT germination and spread, and the local host immune response. We subsequently applied the acquired knowledge to develop a *C. novyi*-NT therapy in an orthotopic rabbit brain tumor model. We found that local accumulation of granular leukocytes, mainly neutrophils, could impede the spread of bacteria through the tumor and prevented complete oncolysis. Depletion of neutrophils using anti-Ly6G antibody or bone marrow suppression using hydroxyurea significantly improved tumor clearance. We then applied this approach to rabbits implanted with an aggressive intracranial brain tumor and achieved long term survival in the majority of animals without apparent toxicity. These results indicated that depleting neutrophils can greatly enhance the safety and efficacy of *C. novyi*-NT cancer therapy for brain tumors and other highly hypoxic tumors.

"Cancer" in a subject refers to characteristics typical of cells that give rise to cancer, such as uncontrolled growth, loss of specialized functions, immortality, prominent metastatic potential, marked increase in anti-apoptotic activity, rapid growth. The presence of cells with growth and proliferation rates, as well as certain characteristic morphologies and cellular markers. In some embodiments, cancer cells become tumor morphology, which may be locally present in the animal or may circulate in the bloodstream as independent cells, such as leukemia cells. Cancers can be head cancer, neck cancer, head and neck cancer, lung cancer, breast cancer, prostate cancer, colorectal cancer, esophageal cancer, gastric cancer, leukemia/lymphoma, uterine cancer, skin cancer, and can include, but is not limited to, endocrine cancer, urological cancer, pancreatic cancer, gastrointestinal cancer, ovarian cancer, cervical cancer, and adenoma. A "tumor," as used herein, refers to any neoplastic cell growth and proliferation, whether malignant or benign, and any pre-cancerous and cancerous cells and tissues. A "solid tumor", as used herein, is an abnormal mass of tissue that generally does not contain cysts or fluid areas. Solid tumors include, by way of non-limiting example, brain, colon, breast, prostate, liver, kidney, lung, esophagus, head and neck, ovary, cervix, stomach, colon, rectum, bladder, uterus, testis, and may be present in the pancreas. In some embodiments, the solid tumor regresses or the growth of the solid tumor is delayed or arrested after the solid tumor is treated with the methods disclosed herein. In other embodiments, the solid tumor is malignant.

Types of tumors which are amenable to treatment according to the methods of the invention and/or using the kits and/or using the compositions of the invention are both solid tumors and hematological cancers. Exemplary tumors include Adrenal Cancer, Anal Cancer, Bile Duct Cancer, Bladder Cancer, Bone Cancer, Brain/CNS Tumors In Adults, Brain/CNS Tumors In Children, Breast Cancer, Breast Cancer In Men, Cancer in Adolescents, Cancer in Children, Cancer in Young Adults, Cancer of Unknown Primary, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, glioblastoma (GBM), Hodgkin Disease, Kaposi Sarcoma, Kidney Cancer, Laryngeal and Hypopharyngeal Cancer, Leukemia, Leukemia—Acute Lymphocytic (ALL) in Adults, Leukemia—Acute Myeloid (AML), Leukemia—Chronic Lymphocytic (CLL), Leukemia—Chronic Myeloid (CIVIL), Leukemia—Chronic Myelomonocytic (CMML), Leukemia in Children, Liver Cancer, Lung Cancer, Lung Cancer—Non-Small Cell, Lung Cancer—Small Cell, Lung Carcinoid Tumor, Lymphoma, Lymphoma of the Skin, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Non-Hodgkin Lymphoma In Children, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma—Adult Soft Tissue Cancer, Skin Cancer, Skin Cancer—Basal and Squamous Cell, Skin Cancer—Melanoma, Skin Cancer—Merkel Cell, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

The following examples are provided to further illustrate the embodiments of the present invention but are not intended to limit the scope of the invention. While they are typical of those that might be used, other procedures, methodologies, or techniques known to those skilled in the art may alternatively be used.

EXAMPLES

Example 1

In this study, based on the observation of leukocyte accumulation around the germination in rat brain tumor, different methods of neutrophil depletion were utilized and the impact on toxicities and tumor clearance was evaluated. The focus was on the deadly glioblastoma, a malignancy arising from the glial tissue in the brain, for which conventional treatment options such as chemotherapy and radiation therapy are limited, with an average life span of 1 to 2 years. When such therapy is applied to the brain, edema might occur due to inflammatory infiltrates, which within the fixed size of the cranial vault may cause fatally raised intracranial pressure. This is particularly challenging in rodents, where the cranial volumes are small (mouse ~440 $mm^3$ and rat 1200 $mm^3$) and animals can easily succumb to brain swelling during germination. For example, the *C. novyi*-NT germination in intracranial GL261 mouse brain tumor can lead to death of the majority of the mice in our experience (unpublished observation). We thus first developed the neutrophil depletion approach using an immunocompetent subcutaneous mouse glioblastoma tumor model and subsequently tested it in a rabbit brain tumor model, whose brain size around 12,000 mm³ offers significant more space to accommodate the swelling than that of a mouse.

Example 2

Materials and Methods

Cell lines and tissue culture: The mouse GL261 glioma cell line was obtained from the German Collection of Microorganisms and Cell Cultures (DSMZ), Germany, and was authenticated by DSMZ. It was maintained in Dulbecco's Modified Eagle Medium (DMEM) media supplemented with 10% fetal bovine serum (FBS) and antibiotics and GL261-luc cells were generated by infection of lentivirus carrying luciferase as described.
Tumor Implantation:

Subcutaneous GL261 tumor: All methods of animal experiments used in this study were in accordance with standards set by the JHU animal care and use committee (ACUC). As we observed an unstable intake rate of subcutaneous GL261 tumor implanted directly from cultured cells into the syngeneic C57BL6 mice, we used serial passaging to maintain the GL261 tumor. To generate the initial tumor, $5 \times 10^6$ GL261-luc cells in 0.1 ml were mixed with equal volume of Matrigel Matrix (BD, Cat. No. 354248) on ice and injected subcutaneously in the flank of a female 6-8 weeks old C57BL6 mouse. Subsequently, the tumor was dissected into 2-3 mm pieces and serially transplanted subcutaneously to generated further flank tumors.
Intracranial VX2 Tumor Male rabbits of 4-6 lbs. were purchased from Robinson Services Inc. Rabbit VX2 tumor was established from a carcinoma induced by the Shope cottontail rabbit papillomavirus (CRPV) and passaged via hind limb donor rabbit as described previously (Parvinian et al. 2014). Briefly, a vial of frozen VX2 cells was defrosted in warm water, centrifuged and injected in the hind leg muscle of a donor New Zealand White rabbit to allow several weeks for the tumor to grow. Rabbits were anesthetized by intramuscular injection of ketamine (50 mg/kg) and xylazine (5-10 mg/kg) and a viable part of tumor within the proliferative rim was excised, minced to small pieces using a scalpel, and dissociated with 1:2 mixture of collagenase (10 mg/ml) and hyaluronidase (1000 unite/ml) in PBS in a flask at 37° C. and 200 rpm rotation. Tumor cells were counted and frozen in DMEM/F12 media supplemented with 10% FBS, antibiotics and 10% DMSO, or used for implantation subsequently. For intracranial implantation, $5 \times 10^5$ VX2 cells in 1.5 µl DMEM/F12 media were injected 10 mm deep, 4 mm right and 3 mm anterior of the bregma. To prevent tumor cell seeding from the needle tract on the brain surface and the meninges around the burr hole, the burr hole was rinsed with 0.5 µg/ul doxorubicin in PBS after needle retraction and inserted with a 3 mm gel stick prepared with 0.25 µg/ul doxorubicin in PBS as described in our previous study (Bai et al. 2017). The burr hole was sealed by bone wax and the scalp was sutured together. Rabbits were monitored for stress signs in eating and fecal patterns in accordance with the JHU ACUC protocol.
Preparation and Intratumoral (IT) Injection of C. novyi-NT Spores
Spore Production and Purification C. novyi-NT spores were produced and purified as previously described (Bettegowda et al. 2006, Roberts et al. 2014). Briefly, bacteria were grown in sporulation medium for two weeks and mature spores were purified through two consecutive Percoll gradients followed by four washes and re-suspensions in PBS. Spores were tested for sterility by culturing product in Soybean-Casein Digest Medium and Thioglycollate Medium (Nelson Laboratories, Salt Lake City, UT). Germination efficiency assays were performed on *Brucella* agar with 5% horse blood. Spores were stored at a concentration of $3 \times 10^9$ spores/ml in sterile PBS at 4° C.
Flank GL261 Tumor Treatment Mice were randomized after tumor implantation before assigned to the control and treatment groups. Prior to IT injection, spores were thoroughly re-suspended with a vortex and taken up in a 10 µl Hamilton syringe with a 32G needle. For the flank GL261 tumor, the injection site was aseptically prepared and a total of 3 µl spores at $6 \times 10^6$/µl were injected in three perceived center locations. The spores were concentrated to reduce the injection volume to minimize the disturbance of local tumor hypoxia and multiple locations were intended to ensure the placement of spores in tumor hypoxic areas. The injection needle was held for 30 sec and removed slowly and the injection site sterilized. To label the tumor hypoxia, GL261 tumor-bearing mice were injected with pimonidazole hydrochloride (PMN, Hydroxyprobe) IP at 60 mg/kg 60 min prior to tumor harvesting and the tumors were preserved immediately in 10% formalin at RT.
Intracranial VX2 Tumor Treatment Rabbits were randomized after tumor implantation before assigned to control and treatment groups. Six days prior to the spore injection, in the HU group, hydroxyurea (HU, Abcam) dissolved in PBS was injected at a dose of 500 mg/kg subcutaneously daily. At the day of spore injection, HU dose was reduced to 100 mg/kg and repeated for another 7 days.

Three days prior to the spore injection, in the CPA group, cyclophosphamide (TCI Chemicals) dissolved in PBS was injected IP at the dose of 125 mg/kg as one-dose pretreatment along with 50 mg/kg Mesna to mitigate CPA's potential urotoxicity.

On day 17 after VX2 tumor implantation, VX2-bearing rabbits were anesthetized and injected with 1 µl C. novyi-NT spores at $6 \times 10^6$/µl in 8.5 mm depth and another 0.5 µl in 6.5 mm depth during needle retraction through the existing burr hole. Dexamethasone sodium phosphate (Matrix Scientific) was injected at a dose of 5 mg/kg subcutaneously at the time of spore injection and repeated daily in the following two days to minimize the risk of edema. Rabbits were observed closely for any signs of deterioration, lethargy, neurotoxicity, or pain in accordance with the Johns Hopkins Animal Care and Use Guidelines.
Hematological Analysis Mouse and rabbit blood were mixed with 5 mM EDTA and analyzed by a ProCyte Dx Hematology Analyzer.

Immunohistochemistry and immunofluorescence staining: Tumors and rabbit brains were preserved in 10% formalin and paraffin sections were obtained. Gram-stained slides, counter-stained with safranin, and H&E-slides were prepared according to routine histopathologic practices. Paraffin section of tumors were deparaffinized, rehydrated and antigen-retrieved using the Citra buffer (Biogenex) as described (Bai et al. 2015). Immunohistochemistry (IHC) staining of PMN-labeled sections followed the procedure established before using monoclonal Hypoxyprobe-1 antibody (Hypoxyprobe Inc.), biotin-conjugated F(ab')2 (JacksonImmunoResearch, 315-066-047) and streptavidin peroxidase (Biogenex HK330-9KT) (Raleigh et al. 1998).

Immunofluorescence staining was performed using mouse anti-Ly6G 1A8 antibody (BD), mouse anti-PMN Hypoxyprobe-1 antibody (Hypoxyprobe Inc.), or rabbit anti- C. novyi-NT antiserum that was obtained from a rabbit with C. novyi-NT germination in the leg VX2 tumor. Antimyeloperoxidase (MPO) antibody (R&D Systems, AF3667) was used in IHC with biotin-conjugated donkey antigoat F(ab')2 (JacksonImmunoResearch, 705-066-147) and streptavidin peroxidase (Biogenex HK330-9KT). Anti-rabbit Alexa 488 and anti-mouse Alexa 594 (Invitrogen) secondary antibodies were applied and 4',6-diamidino-2-phenylindole (DAPI, Vector Laboratories) stained the nuclei, following the procedure described previously (Bai et al. 2015).

Statistical Analysis: Results are presented as a mean value±standard deviation. P values were determined by a Mantel-Cox test and P values <0.05 were deemed as statistically significant. Survival was plotted on Kaplan-Meier curve. Data were analyzed by GraphPad Prism, version 5.0.

Example 3

Results and Discussion
Neutrophil Accumulation and Depletion in C. novyi-NT Therapy of Subcutaneous GL261 Tumor The neutrophils are the final effector cells of the innate immunity and a major phagocyte in host defense against bacterial pathogen. Neutrophils migrate to the site of infection and use a combination of antimicrobial utilities such as cytotoxic granule contents, antimicrobial peptides, reactive oxygen species (ROS), and neutrophil extracellular traps (NETs) to generate a highly lethal antibacterial environment. In our study, mouse GL261 glioma cells were implanted in C57BL6 mice subcutaneously and when the tumors reached the sizes of 400-500 mm$^3$, 2×10$^7$ C. novyi-NT spores were injected into three different central areas of the tumor body. This tumor size was selected to ensure consistent C. novyi-NT germination as we observed inconsistent germination in smaller tumor in this model (data not shown). Mice were observed for tumor swelling and hemorrhagic necrosis, and signs for toxicity. Tumors were harvested 24 hrs after the spore injection and staining via H&E and Gram demonstrated extensive germination, accompanied by marked accumulation of polymorphonuclear granulocytes located between the germinating bacteria and remaining viable tumor, mainly around the outer rim area (FIG. 7A). The cell membrane antigen Ly6G is expressed in granulocytes and transiently in some monocytes and is a well defined marker for murine neutrophils, especially the circulating and recruited neutrophils. Immunofluorescence staining of 1A8 anti-Ly6G antibody identified the majority of those cells as neutrophils (FIG. 7A). Those immune cells could be depleted by treating the mice with 1A8 antibody intraperitoneally (IP) 24 hrs before the spore injection (FIG. 1B, FIG. 7B). Staining with anti-CD11b and CD3 antibodies revealed minimal numbers of positive cells among those accumulated immune cells (FIGS. 8A and 8B). Similar depletion was achieved also by daily IP injection of hydroxyurea (HU), an immunosuppressant used in treating myeloproliferative diseases, for 5 days before the spore injection, as indicated by the complete blood count (CBC) of mouse blood (FIG. 1C). The counts of blood cells with the suppression by HU showed also a significant drop of lymphocytes (FIG. 8C). Previous studies have demonstrated substantial mortality rates of C. novyi-NT-treated mice with large subcutaneous CT26 and GL261 tumors (~700 mm$^3$ or 600-900 mm$^3$). In this study, we used moderate tumor sizes and while germination occurred in all tumors, 2 out of 11 mice (2/11) died of treatment-related toxicity within 48 hrs. Of the surviving animals, 8 mice with initial tumor reduction were found later to have tumor regrowth (partial), and 1 mouse was completely cured as determined by absence of any tumor after 3 weeks (FIG. 1D). In contrast, in the cohorts treated with anti-Ly6G 1A8 antibody or HU, 11/15 or 9/12 mice respectively were cured of tumor, 2/15 or 1/12 were partial, and 2/15 or 2/12 died from immediate toxicities, respectively (FIG. 1D). HU or 1A8 antibody alone did not show any noticeable therapeutic effects (data not shown). Bioluminescence imaging of the luciferase-labeled tumor illustrated these therapeutic outcomes (FIG. 1E).

Tumor Hypoxia and a Model of C. novyi-NT Germination

While these results demonstrated the essential role of neutrophil defense in preventing complete tumor clearance by C. novyi-NT, they raised the question of how the clearance of whole tumor was achieved as the tumor outer rim areas, which are distant from the necrotic centers and close to blood vessels, are regarded as non-hypoxic in a number of tumor models. In order to investigate the spatial distribution of hypoxia in the flank GL261 tumor, we labeled the tumor with a hypoxia indicator pimonidazole (PMN) via IP injection 90 min before harvesting the tumor. Immunohistochemistry staining of PMN using Hypoxyprobe-1 monoclonal antibody (Mab) that stains tissues with a partial 02 pressure below 10 mmHg, showed a distribution of small hypoxic pockets throughout the tumor rim areas adjacent to surrounding tissues (FIG. 2A). Numerous apparent tumor vessels were also stained positive of bound PMN as exemplified in FIG. 2A and FIG. 9. This distribution pattern of tumor hypoxia was also illustrated by the immunofluorescence (IF) staining of PMN using the same Hypoxyprobe-1 Mab (FIG. 2B). Next, we attempted to visualize the germination process in a time course after C. novyi-NT spore injection in GL261 tumor pretreated with anti-Ly6G antibody for neutrophil depletion. At 6, 8, and 12 hrs following spore injection, GL261 tumors were harvested after 1 hr of PMN labeling. No significant germination was observed in the 3 harvested tumors at 6 hrs (data not shown). After 8 hrs, germination could be determined in some areas of the tumor via IF using rabbit anti-C. novyi-NT antibody. In FIG. 2C, a presumed initial germination site was observed in higher magnification, where the spores, stained as green dots, were found among cell aggregates which were likely accumulated immune cells, surrounded by hypoxic tumor cells stained in red (FIG. 2C). Some germinating bacteria in the rod form were found co-localized with hypoxic tumor cells (FIG. 2C, white arrow head). Macroscopic view of tumors 12 hrs after the spore injection revealed a germination pattern, which appeared to spread from one large germinated area to adjacent small hypoxic pockets (FIGS. 2D and 2E). Pictures of higher magnifications showed that individual C. novyi-NT bacteria were distributed sparsely in the surrounding tumor tissue of a germination area, some of which were found within a hypoxic pocket (FIG. 3A) and initial colonization occurred in such hypoxic pockets (FIGS. 3B-D). Based on this observation, a germination and spreading mechanism has emerged, in which the injected spores germinate first in a hypoxic/necrotic area, then the bacteria powered by flagellum movement randomly migrate into the vicinity to find another hypoxic pocket which they colonize and form a new germination center. In the absence of the intervention of neutrophils, within several hours, ever expanding germination fronts supported by hypoxic pockets presented throughout the tumor body and rim inevitably leading to total destruction of tumor tissue.

C. novyi-NT Therapy of Orthotopic VX2 Rabbit Brain Tumor

Figure 10:
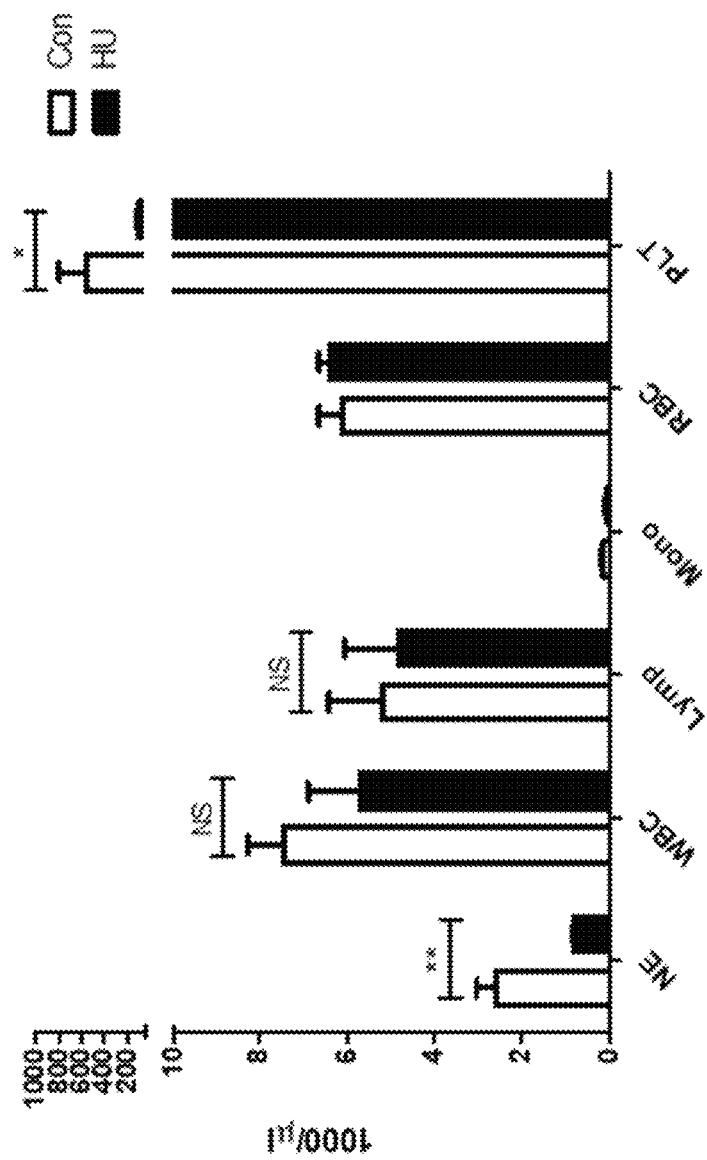

Rabbit VX2 tumor was established from a carcinoma induced by the Shope cottontail rabbit papillomavirus (CRPV) and has been widely used as a rabbit intracranial tumor model for various imaging and therapeutic studies. As detailed in the Introduction, we chose the rabbit model to study C. novyi-NT germination for the larger cranial size. VX2 tumor cells were implanted in the right frontal lobe and rabbits became symptomatic with a tilted head, severe reduction of eating and fecal output at day 20-25 after the tumor implantation, which necessitated euthanasia, resulting in a median survival of 21 days for untreated animals (FIG. 5D). C. novyi-NT treatment was initiated relatively late at day 17 after tumor implantation to ensure that a sizable tumor had formed which is needed for IT spore injection to support a robust germination. Histologically, VX2 brain tumor resembled some key features of human glioblastoma, such as necrotic centers and invasive growth pattern observed as small tumor satellites in the surrounding brain tissues (FIGS. 4B and 4C). C. novyi-NT germination in the tumor led to sizable accumulation of neutrophils that prevented bacteria from completely disseminating to the remaining tumor and particularly the outer rim (FIG. 4D). Pre-treatment of rabbits with HU, similar as observed with GL261 model before, was effective in suppressing the intratumoral accumulation of neutrophils, which led to enhanced bacterial tumor eradication. Gram staining of a brain section from a HU-pretreated rabbit 72 hrs after the spore injection revealed an apparent complete tumor clearance with a germinating front (FIG. 5A). Within the surrounding brain tissue, some tumor vessel structures and invading satellites were colonized by C. novyi-NT (FIG. 5B). Due to the lack of available antibody targeting rabbit neutrophils, we compared cyclophosphamide (CPA) and HU for their efficacies in neutrophil depletion. Although both CPA and HU could achieve significant neutrophil suppression, neutrophil counts quickly rebounded within 2 days after spore injection in the CPA cohort, while the rabbits pretreated by HU maintained lower neutrophil counts for at least 3 days after spore injection (FIG. 5C), thereby providing a potential therapeutic window for tumor eradication. At the administered dose, the HU-induced neutrophil suppression was fairly specific as lymphocyte counts were not significantly affected by HU; however, platelets showed a marked drop (FIG. 10). Pretreatment with HU significantly improved the therapeutic efficacy and safety of IT C. novyi-NT therapy and resulted in 8 long-term survivors out of 9 rabbits, with one death owing to tumor regrowth 26 days after spore injection as determined by autopsy and brain sections (FIG. 5D). In comparison, among 6 rabbits injected with C. novyi-NT spores alone without pretreatment, 4 died from immediate toxicities within 2 days, 1 died from tumor regrowth 19 days after spore injection and 1 rabbit achieved long-term survival until euthanized in a healthy condition 342 days after tumor implantation (FIG. 5D). The cohort pretreated with CPA prior to spore injection was inferior to HU and achieved similar results as observed in the C. novyi-NT alone cohort without any long-term survivor.

Next, we closely examined the rabbits' brain sections in the various treatment regimens. An example of VX2 brain tumor section at the day of C. novyi-NT treatment is shown in FIG. 6A. The brain section of a rabbit that died one day after the spore injection without neutrophil depletion revealed a severely hemorrhagic and expanded lesion with considerable mass effect due to edema compared to the contralateral brain structure (FIG. 6B). This stands in contrast to a "transformed" lesion (black arrow) of a HU-pretreated rabbit sacrificed in healthy condition 8 days after spore injection (FIG. 6C), which upon closer examination was free of tumor and germinating bacteria but predominantly filled with neutrophils as demonstrated by antimyeloperoxidase (MPO) IHC (brown) (FIG. 6D, FIGS. 11A and 11B). MPO can be released into the surrounding by neutrophils during degranulation to facilitate the killing of bacteria. Of note, neutrophil counts made a rebound around day 3-7 after the C. novyi-NT spore injection (FIG. 5C). As a minority of rabbits in the C. novyi-NT alone group survived the initial germination and died from tumor regrowth (FIG. 5D), we sacrificed another otherwise healthy rabbit on this regimen 8 days after spore injection and observed a restricted lesion filled with neutrophils without germinating bacteria (FIGS. 12A and 12B), however pockets of growing tumor in the former tumor-brain transitional areas were discovered, indicating a partial tumor clearance (FIGS. 12C and 12D).

Discussion

In adoptive T cell therapies, preconditioning by lymphodepletion has been incorporated in the treatment protocol to achieve optimal efficacies, which includes using chemotherapeutics such as fludarabine and cyclophosphamide or full-body radiation. This is presumably facilitated by eliminating regulatory T cells and competing elements of the immune system, which help prolong the persistence of infused cells. In oncolytic virus therapies, preconditioning with immune modulators or complement depletion successfully improved the viral targeting of tumors. So far, immune-modulating pretreatment has not been used in therapies with oncolytic bacteria.

In this study, we reported the development of a combination therapy of C. novyi-NT and neutrophil reduction, with reduced cytotoxicity and substantially enhanced antineoplastic potency in the orthotopic rabbit brain tumor model and with enhanced efficacy in a subcutaneous mouse glioma model. Neutrophils were rapidly recruited to the tumor sites in response to C. novyi-NT germination and the accumulation of neutrophils inside the tumor caused a barrier that limited the bacterial spread. Drug-induced suppression or antibody-mediated depletion of neutrophils permitted the bacteria to replicate and spread within the tumors unhindered and subsequently, led to considerably enhanced tumor clearance. Importantly, over 70% of animals treated with such combination showed no evidence of tumor recurrence and remained alive compared to <10% in the control. In the orthotopic rabbit brain tumor mode, HU pretreatment also significantly reduced C. novyi-NT-induced toxicity which may be related to the suppression of the myeloid cell populations that are responsible for the release of acute inflammatory cytokines. In animals with tumor recurrence, we suspect that C. novyi-NT could not effectively colonize the peritumoral regions, which are less hypoxic. Those well-vascularized tumor regions are susceptible to chemotherapeutic drugs, and thus the combinatorial use of these agents may further improve the treatment efficacy. Although the effectiveness of inflammation suppression to substantially enhance the oncolytic potency was only evaluated in one bacterium, its general applicability to other types of oncolytic bacteria is likely but will need to be validated in relevant animal models. It is worth mentioning that in oncolytic viral therapies, local inflammation and infiltration of immune cells in the tumor tissue are desired and vital for immunogenic killing of the tumor.

It is notable that the neutrophil-suppressing pretreatment reduced the toxicity-related death in the orthotopic rabbit brain tumor model (4 out of 6 in *C. novyi*-NT only group vs 0 out of 9 in *C. novyi*-NT plus HU group in FIG. 5D), while low but largely unchanged toxicity-related death rates were observed in the subcutaneous GL261 mouse model with or without pretreatment (FIG. 1D). The rapid rise of intracranial pressure in the VX2 brain tumor model during germination was likely the main cause of toxicity-related death and a reduction of brain edema indicated by the less inflammatory lesion (FIG. 6C) via suppression of neutrophils has a very sensitive effect on mitigating the animal mortality. Less local infiltration and accumulation of neutrophils and possibly other myeloid cells suppressed by HU may have contributed to the edema reduction and improved safety.

Hypoxia in solid tumor arises in regions with insufficient oxygen supply, which, in the general view, is attributed principally to the distance to blood vessels. However, in tumors such as glioblastoma, where vasculatures are often disorganized and dysfunctional, and a small percentage of vascular endothelium could be of neoplastic origin, local hypoxia may not necessarily be determined by the distance to the blood vessels. Of note, in human glioblastomas and high-grade astocytomas, oxygen pressure was measured at 9.2±5.8 mmHg or 15.3±2.3 mmHg in intratumoral locations, at 17.9±9.3 mmHg in peritumoral areas and at 59.8±6.5 mmHg in the brain tissue, which is consistent with the PMN staining in this study that labels tissues with oxygen pressure below 10 mmHg. *C. novyi* can achieve full germination below the oxygen pressure of 7.6 mmHg and tolerate up to 15.2 mmHg. The mouse tumor model in this study was established from subcutaneously implanted GL261 glioblastoma cell line and the PMN-mediated staining revealed a wide distribution of relatively small hypoxic pockets throughout the viable tumor, including the tumor rim. The biological functionality of those hypoxic pockets was essentially validated by focused colonization of germinating *C. novyi*-NT bacteria. Interestingly, multiple tumor vascular structures were also stained positive of hypoxia, underlying their dysfunctionality. In fact, the origin of tumor hypoxia may involve multiple and complex factors, including hyper respiratory activity in mitochondria as an intrinsic hypoxia generator in the tumor cells. Such intrinsic tumor hypoxia has been measured inconsistently and may vary greatly among different types of tumor cells, generally correlating with the aggressiveness of the tumor, consistent with our unpublished observation. This could indeed present a challenge to therapeutics targeting tumor hypoxia, including *C. novyi*-NT, in a broad application of different tumor types. When used in treating aggressive brain tumor, however, *C. novyi*-NT demonstrated promising therapeutic efficacies once we incorporated modulation of immune response to ensure the spread of the bacteria and to reduce side effects. These improvements may lead to the development of safer and more effective oncolytic bacterial treatments for patients with glioblastomas and other poorly vascularized tumors in the future.

Although the invention has been described with reference to the above examples, it will be understood that modifications and variations are encompassed within the spirit and scope of the invention. Accordingly, the invention is limited only by the following claims.

The following are illustrative embodiments of the present disclosure:

1. A method of treating cancer in a subject comprising:
    a) administering to the subject hydroxyurea (HU), cyclophosphamide, or a combination thereof: and
    b) an anaerobic bacterium,
thereby treating cancer in the subject.

2. The method of claim 1, wherein the anaerobic bacterium is *Clostridium novyi*.
3. The method of claim 1, wherein the anaerobic bacterium is a toxin-depleted anaerobic bacterium.
4. The method of claim 3, wherein the toxin-depleted anaerobic bacterium is *Clostridium novyi*-NT (*C. novyi*-NT).
5. The method of claim 1, wherein a combination of the hydroxyurea (HU), the cyclophosphamide, or a combination thereof and the anerobic bacteria is administered sequentially or concurrently.
6. The method of claim 1, wherein the method further comprising administering the hydroxyurea (HU), cyclophosphamide, or combinations thereof from about 10-72 hours prior to administering the anaerobic bacterium.
7. The method of claim 6, wherein the administration is from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, or 72 hours prior to administering the anaerobic bacterium.
8. The method of claim 1, wherein the cancer is glioblastoma (GBM).
9. A method of treating cancer in a subject comprising:
    (a) administering to the subject at least one immunoregulatory compound; and
    (b) administering at least one anaerobic species of bacteria, thereby treating cancer in the subject.
10. The method claim 9, wherein the cancer is a solid tumor.
11. The method of claim 9, wherein the cancer is brain, colon, breast, prostate, liver, kidney, lung, esophagus, head and neck, ovary, cervix, stomach, colon, rectum, bladder, uterus, testis, or pancreatic cancer.
12. The method of claim 11, wherein the cancer is brain cancer.
13. The method of claim 9, wherein the at least one immunoregulatory compound is selected from the group consisting of cyclophosphamide, hydroxyurea, prednisone, methylprednisolone, dexamethasone, colchicine, hydroxychloroquine, sulfasalazine, and dapsone,
14. The method of claim 9, wherein the at least one immunoregulatory compound is selected from the group consisting of infliximab, adalimumab, golimumab, etanercept, certolizumab, tocilizumab, sarilumab, eculizumab, secukinumab, ixekizumab, brodalumab, and guselkumab.
15. The method of claim 9, wherein the immunoregulatory compound is administered to the subject from about 1, 2, 3, 4, 5, 6, 7, 8, 9, or 10 days prior to administering the anaerobic species of bacteria.
16. The method of claim 15, wherein the immunoregulatory compound is administered to the subject at a reduced dose for about 1, 2, 3, 4, 5, 6, 7, 8, 9, or 10 days after administering the anaerobic species of bacteria.
17. The method of claim 15, wherein the immunoregulatory compound is cyclophosphamide.
18. The method of claim 17, wherein the cyclophosphamide is administered at a dose of about 1 mg/kg, 10 mg/kg, 20 mg/kg, 25 mg/kg, 50 mg/kg, 75 mg/kg, 100 mg/kg, or 125 mg/kg per day.
19. The method of claim 17, wherein the cyclophosphamide is administered with at least one antineoplastic detoxifying agent.
20. The method of claim 19, wherein the antineoplastic detoxifying agent is Mesna.

21. The method of claim 20, wherein the Mesna is administered at a dose of about 1 mg/kg, 10 mg/kg, 20 mg/kg, 30 mg/kg, 40 mg/kg, or 50 mg/kg per day.

22. The method of claim 13, wherein the immunoregulatory compound is hydroxyurea.

23. The method of claim 22, wherein the hydroxyurea is administered at a dose of about 1 mg/kg, 10 mg/kg, 20 mg/kg, 25 mg/kg, 30 mg/kg, 40 mg/kg, 50 mg/kg, 75 mg/kg, 100 mg/kg, 200 mg/kg, 300 mg/kg, 400 mg/kg, or 500 mg/kg per day.

24. The method of claim 9, wherein the at least one anaerobic species of bacteria is selected from the group consisting of *Salmonella* ssp., *Klebsiella* ssp., *Escherichia* ssp., *Caulobacter* ssp., *Listeria* ssp., *Bifidobacterium* ssp., *Clostridium* ssp., *Streptococcus* ssp., *Lactobacillus* ssp., *Mycobacterium* ssp., and *Proteus* ssp.

25. The method of claim 24, wherein the at least one anaerobic species of bacteria is *Clostridium novyi* or *Clostridium sordellii*.

26. The method of claim 25, wherein the anaerobic species of bacteria is *Clostridium novyi*.

27. The method of claim 9, wherein the at least one anaerobic species of bacteria is a toxin-depleted species of anaerobic bacteria.

28. The method of claim 27, wherein the toxin-depleted species of anaerobic bacteria is *C. novyi*-NT.

29. The method of claim 28, wherein an effective amount of *C. novyi*-NT spores is administered to the patient by injection into the tumor.

30. The method of claim 9, wherein an immunoregulatory compound is injected subcutaneously at the time of spore injection.

31. The method of claim 13, wherein the immunoregulatory compound is dexamethasone sodium phosphate.

32. A method for treating a solid tumor in a subject comprising:
a) administering to the subject hydroxyurea (HU), cyclophosphamide, or a combination thereof, and
b) an anerobic bacterium,
thereby treating the solid tumor in the subject.

Although the invention has been described with reference to the above examples, it will be understood that modifications and variations are encompassed within the spirit and scope of the invention. Accordingly, the invention is limited only by the following claims.

What is claimed is:

1. A method of treating a solid tumor in a subject comprising:
(a) administering to the subject at least one immunoregulatory compound selected from at least one of an anti-neutrophil antibody, hydroxyurea, or cyclophosphamide; and
(b) administering at least one anaerobic species of bacteria,
wherein the at least one immunoregulatory compound is administered prior to administering the anaerobic species of bacteria,
thereby treating the solid tumor in the subject.

2. The method of claim 1, wherein the solid tumor is brain, colon, breast, prostate, liver, kidney, lung, esophagus, head and neck, ovary, cervix, stomach, colon, rectum, bladder, uterus, testis, or pancreatic cancer.

3. The method of claim 2, wherein the solid tumor is brain cancer.

4. The method of claim 1, further comprising administering prednisone, methylprednisolone, dexamethasone, colchicine, hydroxychloroquine, sulfasalazine, infliximab, adalimumab, golimumab, etanercept, certolizumab, tocilizumab, sarilumab, eculizumab, secukinumab, ixekizumab, brodalumab, guselkumab, or dapsone with the immunomodulatory compound.

5. The method of claim 1, wherein the immunoregulatory compound is administered to the subject from about 1, 2, 3, 4, 5, 6, 7, 8, 9, or 10 days prior to administering the anaerobic species of bacteria.

6. The method of claim 5, wherein the immunoregulatory compound is administered to the subject at a reduced dose for about 1, 2, 3, 4, 5, 6, 7, 8, 9, or 10 days after administering the anaerobic species of bacteria.

7. The method of claim 1, wherein the immunoregulatory compound is cyclophosphamide or hydroxyurea.

8. The method of claim 7, wherein the cyclophosphamide or hydroxyurea is administered at a dose of about 0.1 mg/kg, 1 mg/kg, 10 mg/kg, 20 mg/kg, 25 mg/kg, 50 mg/kg, 75 mg/kg, 100 mg/kg, 125 mg/kg, 150 mg/kg, 200 mg/kg, 300 mg/kg, 400 mg/kg or 500 mg/kg per day.

9. The method of claim 7, wherein the cyclophosphamide is administered with at least one antineoplastic detoxifying agent.

10. The method of claim 1, wherein the anti-neutrophil antibody is an anti-Ly6G antibody.

11. The method of claim 1, wherein the immunoregulatory compound is administered to the subject from about 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, or 72 hours prior to administering the anaerobic species of bacteria.

* * * * *